(12) United States Patent
Kung et al.

(10) Patent No.: US 7,067,249 B2
(45) Date of Patent: Jun. 27, 2006

(54) INHIBITION OF HEPATITIS B VIRUS (HBV) REPLICATION BY RNA INTERFERENCE

(75) Inventors: Hsiang-Fu Kung, Hong Kong (CN); Ming-Liang He, Hong Kong (CN)

(73) Assignee: The University of Hong Kong, Hong Kong (CN)

(*) Notice: Subject to any disclaimer, the term of this patent is extended or adjusted under 35 U.S.C. 154(b) by 0 days.

(21) Appl. No.: 10/848,736

(22) Filed: May 19, 2004

(65) Prior Publication Data

US 2004/0235775 A1 Nov. 25, 2004

Related U.S. Application Data

(60) Provisional application No. 60/471,903, filed on May 19, 2003.

(51) Int. Cl.
*C07H 21/04* (2006.01)
(52) U.S. Cl. ............... 435/5; 536/24.3; 536/24.32; 536/23.1; 435/320.1
(58) Field of Classification Search ............... 424/93.2; 514/44; 536/23.1, 24.3, 24.32; 435/5, 320.1
See application file for complete search history.

(56) References Cited

U.S. PATENT DOCUMENTS

2003/0206887 A1* 11/2003 Morrissey et al. ......... 424/93.2

* cited by examiner

*Primary Examiner*—Jeffrey Stucker
*Assistant Examiner*—Bo Peng
(74) *Attorney, Agent, or Firm*—Dickstein, Shapiro, Morin & Oshinsky, LLP.

(57) ABSTRACT

The present invention relates to the inhibition of Hepatitis B virus (HBV) replication by RNA molecules of the present invention. Specifically, the RNA molecules of the present invention are double-stranded ribonucleic acid molecules (dsRNA). Specifically, the invention relates to small interfering RNAs (siRNA) which are double-stranded RNAs that direct the sequence-specific degradation of messenger RNA in mammalian cells. The invention relates to development of a new anti-HBV therapy by inhibition of Hepatitis B Virus (HBV) replication using stably-expressed short hairpin RNAs (shRNA), which degrade HBV pregenomic RNA and message RNAs. Included are methods of treatment of cancer by the administration of RNA molecules of the present invention in combination with surgery, alone or in further combination with standard and experimental chemotherapies, hormonal therapies, biological therapies/immunotherapies and/or radiation therapies.

9 Claims, 3 Drawing Sheets

INHIBITION OF HEPATITIS B VIRUS (HBV) REPLICATION BY RNA INTERFERENCE

Figure 1A:
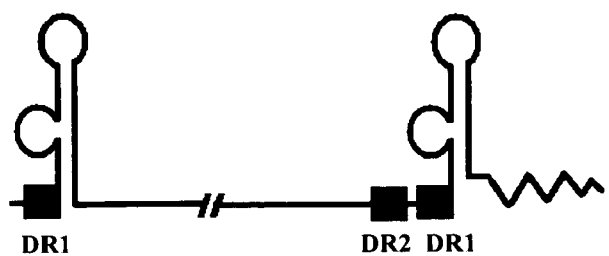

This application claims priority benefit to U.S. provisional application No. 60/471,903, filed May 19, 2003, which is incorporated herein by reference in its entirety.

1. INTRODUCTION

The present invention relates to the inhibition of Hepatitis B virus (HBV) replication by RNA molecules of the present invention. Specifically, the RNA molecules of the present invention are double-stranded ribonucleic acid molecules (dsRNA). Specifically, the invention relates to small interfering RNAs (siRNA) which are double-stranded RNAs that direct the sequence-specific degradation of messenger RNA in mammalian cells. The invention relates to development of a new anti-HBV therapy by inhibition of Hepatitis B Virus (HBV) replication using stably-expressed short hairpin RNAs (shRNA), which degrade HBV pregenomic RNA and message RNAs. Included are methods of treatment of cancer by the administration of RNA molecules of the present invention in combination with surgery, alone or in further combination with standard and experimental chemotherapies, hormonal therapies, biological therapies/immunotherapies and/or radiation therapies.

2. BACKGROUND OF THE INVENTION

The major challenges for anti-HBV therapy are the low efficacy of current drugs and the occurrence of drug resistant HBV mutations. Lau, 2001, Clin Liver Dis. 5:361–379. There are an estimated 400 million chronic Hepatitis B virus (HBV) infected patients worldwide, and over one million people die of liver failure or HBV-associated hepatocellular carcinoma (HCC) annually. The major challenges for anti-HBV therapy are the low efficacy of current drugs and the occurrence of drug resistant HBV mutations. Only about twenty percent of the patients benefit from combination therapy with interferon-alpha and lamuvidine. It is therefore important to develop a new strategy to treat HBV patients. A drug with new target sites or independent metabolic pathways may overcome these shortcomings.

3. SUMMARY

The present invention is based on the observation of the present inventors that stably-expressed 21-mer short hairpin RNAs (shRNA) inhibit Hepatitis B Virus (HBV) replication. shRNA degrade targets such as HBV pregenomic RNA and message RNAs. These targets include HBV reverse-transcriptase and other sites of pregenomic RNA, including DR elements, S, and X gene. In specific embodiments, shRNAs specifically target drug binding sites (736i), the open reading frame of S antigene, polymerase (157i), the open reading frame of X protein (1694i), the DR elements on the pregenomic RNA (1592i and 1826i), or block HBV replication. The anti-HBV efficacy of siRNA is much more potent than that of lamivudine. The present inventors discovered that shRNAs can serve as efficient anti-HBV agents. The inventors also discovered that shRNAs provide synergistic effects on the inhibition of HBV replication due to different mechanisms of drug actions. In some embodiments, shRNA may be combined with current anti-HBV drugs to increase the anti-HBV efficacy. In a specific embodiment, shRNA may be combined with lamivudine and/or interferon alpha for the treatment of HBV related diseases. In other preferred embodiments, shRNAs may be used in combination with other therapy such as, but not limited to, chemotherapy or therapies using nucleotide analogs. Accordingly, the present invention also provides methods of treatment for liver failure or HVB-associated hepatocellular carcinoma (HCC). In specific embodiments, shRNAs may be mediated by viral gene delivery vector. In a specific embodiment, shRNAs may be mediated via gene therapy.

In certain embodiments, a process is provided for inhibiting expression of a target gene in hepatitis B virus. The process comprises introduction of RNA with partial or fully double-stranded character into the cell affected by the virus or into the extracellular environment. Inhibition is specific in that a nucleotide sequence from a portion of the target gene is chosen to produce inhibitory RNA. The present invention is effective in producing inhibition of gene expression, specific to the targeted gene, and allowing inhibition of many different types of target gene in HBV.

Depending on the particular target gene and the dose of double stranded RNA material delivered, the method of the invention may provide partial or complete loss of function for the target gene of HBV. A reduction or loss of gene expression may be at least 99%, 90%, 85%, 80%, 75%, 70%, 65%, 60%, 55%, 50%, 45%, 40%, 45%, 35%, 30%, 25%, 20%, 15%, 10%, 5% of the HBV target gene expression. Quantitation of gene expression in a cell may show inhibition at the level of accumulation of target mRNA or translation of target protein.

The RNA molecules of the present invention may comprise one or more strands of polymerized ribonucleotides; it may include modifications to either the phosphate-sugar backbone or the nucleoside. The double-stranded structure may be formed by a single self-complementary RNA strand or two complementary RNA strands. RNA duplex formation may be initiated either inside or outside the infected cell. The RNA may be introduced in an amount which allows delivery of at least one copy per infected cell. Higher doses of double-stranded material may yield more effective inhibition. Inhibition is sequence-specific in that nucleotide sequences corresponding to the duplex region of the RNA are targeted for genetic inhibition. RNA containing a nucleotide sequences identical to a portion of the target gene is preferred for inhibition. RNA sequences with insertions, deletions, and single point mutations relative to the target sequence may be effective for inhibition. Thus, sequence identity may optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript.

The RNA molecules of the present invention may be synthesized either in vivo or in vitro. Endogenous RNA polymerase of the cell infected with HBV may mediate transcription in vivo, or cloned RNA polymerase can be used for transcription in vivo or in vitro. For transcription from a transgene in vivo or via an expression construct, a regulatory region may be used to transcribe the RNA strand (or strands).

The RNA may be directly introduced into the cell (i.e., intracellularly); or introduced extracellularly into a cavity, interstitial space, into the circulation of a subject in need of the treatment.

4. BRIEF DESCRIPTION OF THE DRAWINGS

Figure 1B:
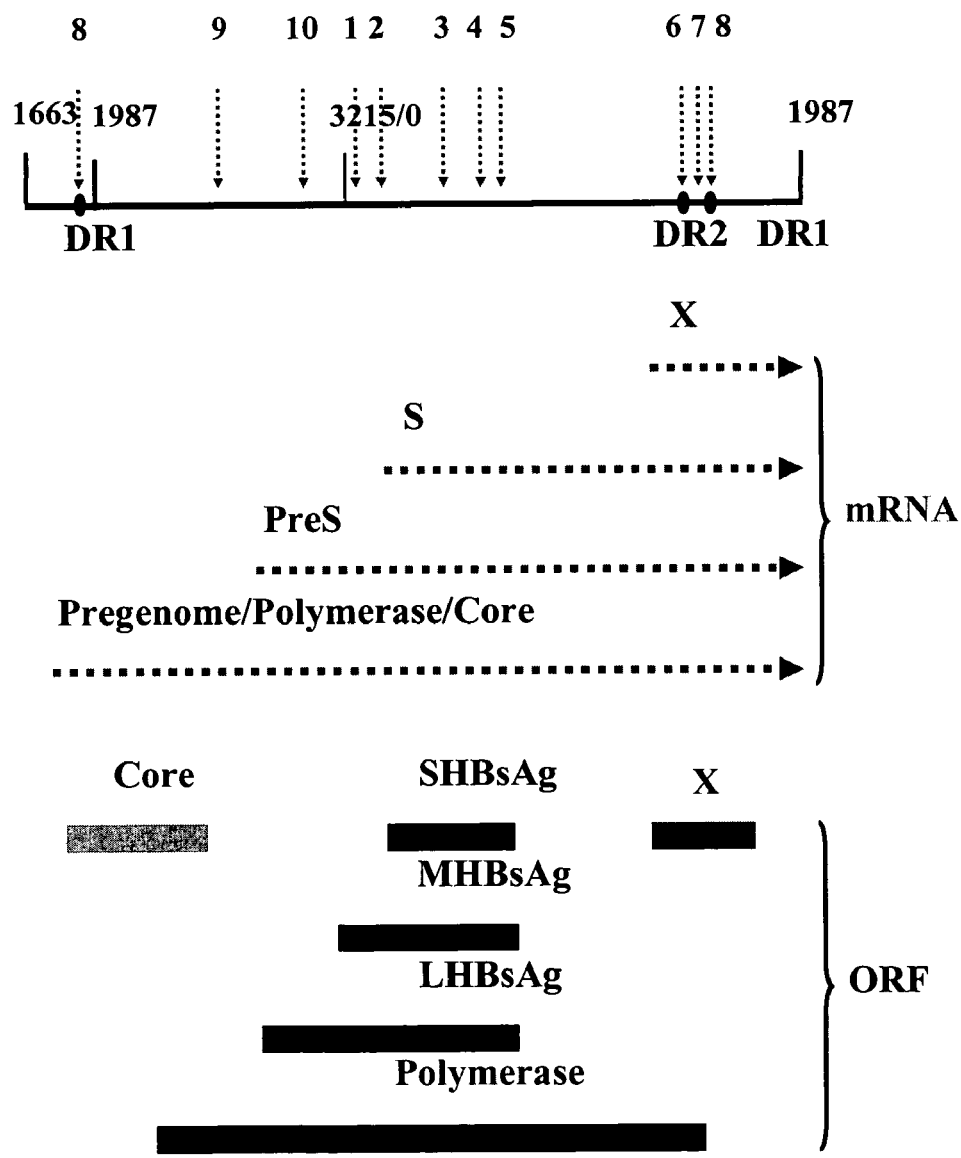

FIGS. 1A & B show the structure of HBV RNA and siRNA target sites. FIG. 1A: HBV pregenomic RNA. DR1 and DR2 play crucial roles in reverse-transcription, viral packaging, primer translocation and in situ priming. Seeger et al., 2000, *Microbiol Mol Biol Rev* 64:51–68. FIG. 1B: HBV RNA species and siRNA target sites. The pregenomic RNA codes for core antigen and reverse-transcriptase, and PreS mRNA codes for large surface antigen (LHBsAg) and middle surface antigen (MHBsAg). The siRNA target sites are shown by arrows. 1, 87i; 2, 157i; 3, 451i; 4, 660i; 5, 736i; 6, 1592i; 7. 1694i; 8, 1826i; 2310i; 10. 2979i.

Figure 2A:
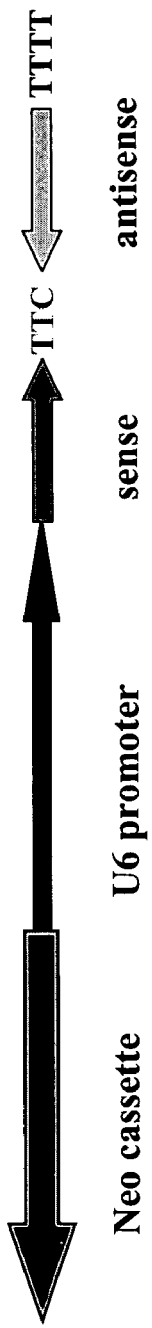
Figure 2B:
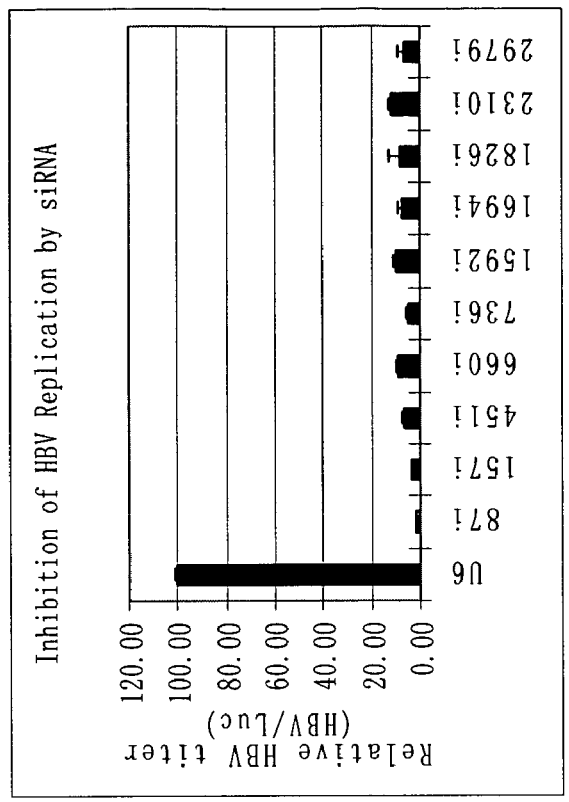
Figure 2C:
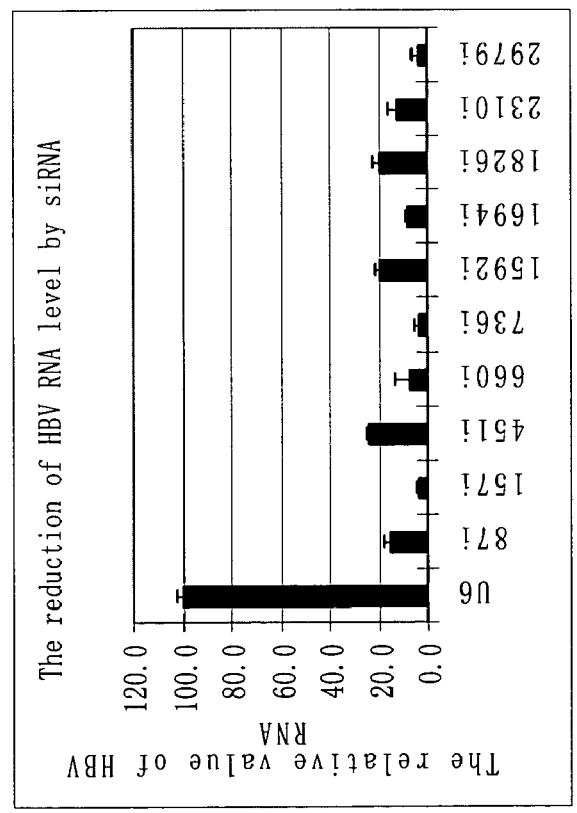

FIGS. 2A–2C show the inhibition of HBV replication by shRNA. FIG. 2A: The construct map for expression of siRNAs. FIG. 2B: The reduction of HBV RNA level by stably-expressed siRNA. The HBV RNA and luciferase mRNA were quantified by real-time RT-PCR. FIG. 2C: The inhibition of HBV replication by stably-expressed siRNAs. The ratio of HBV titer to luciferase activity indicates HBV replication activity.

Figure 3:
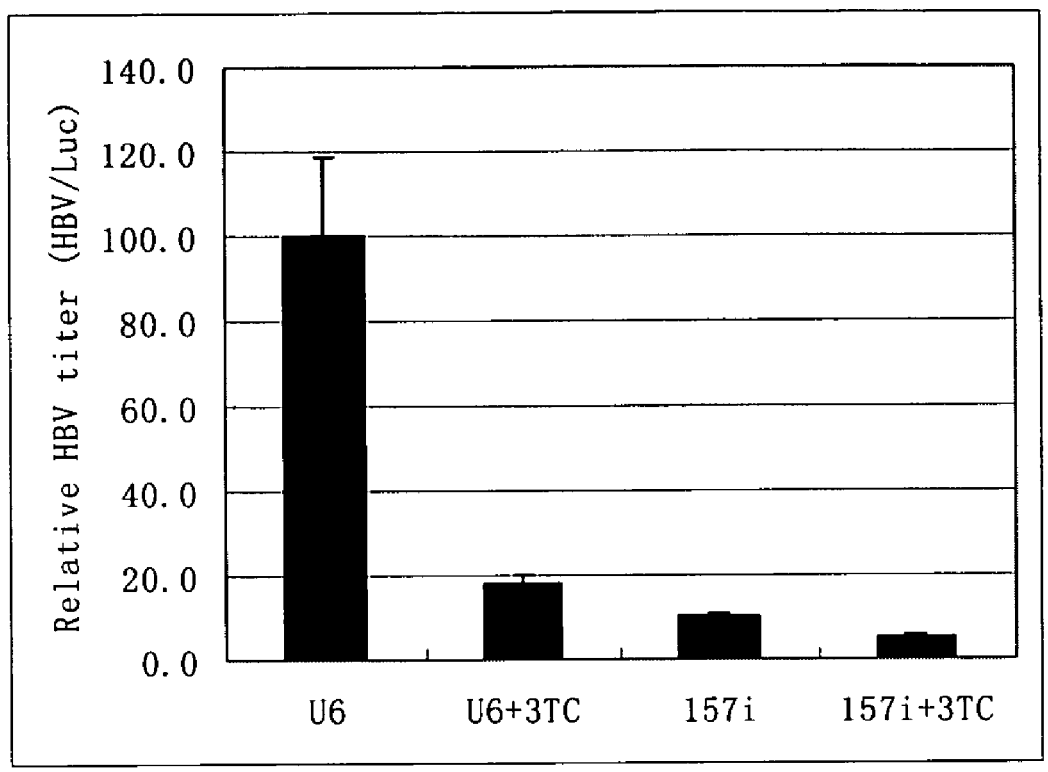

FIG. 3. The synergistic effect of shRNA and lamivudine. A synergistic effect on the inhibition of HBV replication was observed when shRNA stably-expressed cells were cultured in the 3TC containing medium.

5. DETAILED DESCRIPTION

The present invention relates to the inhibition of Hepatitis B virus (HBV) replication using RNA molecules of the present invention. Specifically, the RNA molecules of the present invention are double-stranded ribonucleic acid molecules (dsRNA). Specifically, the invention relates to small interfering RNAs (siRNA) which are double-stranded RNAs that direct the sequence-specific degradation of messenger RNA in mammalian cells. The invention relates to development of a new anti-HBV therapy by inhibition of Hepatitis B Virus (HBV) replication using stably-expressed short hairpin RNAs (shRNA), which degrade HBV pregenomic RNA and message RNAs.

5.1. Inhibition of HBV Genes

Disruption of the HBV life cycle will inhibit HBV replication. Upon infection, the partial double strand DNA of the present invention is repaired to form a 3.2-kb cccDNA, which serves as a template to transcribe overlapping RNA species including a 3.5-kb pregenomic RNA (FIG. 1A) and mRNAs (FIG. 1B) coding for reverse-transcriptase (polymerase), core, PreS, S and X proteins. Seeger et al., 2000, Microbiol. Mol. Biol. Rev. 64:51–68. These RNAs are then translated into HBV proteins or reverse-transcribed into HBV DNA. All the HBV proteins play important roles in HBV transcriptional regulation, viral package, reverse-transcription and viral DNA recycling. During HBV replication, the special structure DR1 and DR2 (FIG. 1A) in the pregenomic RNA are the essential cis-elements for viral package, primer translocation and reverse-transcription.

RNAi regulates gene expression via a ubiquitous mechanism by degradation of target mRNA in a sequence-specific manner. McManus et al., 2002, Nat Rev Genet 3:737–747. In mammalian cells, interfering RNA (RNAi) can be triggered by 21- to 23-nucleotide duplexes of siRNA. Lee et al., 2002, Nat Biotechnol 20: 500–505; Paul et al., 2002, Nat Biotechnol. 20:505–508; Miyagishi et al., 2002, Nat Biotechnol. 20:497–500; Paddison et al., 2002, Genes Dev. 16: 948–958. The expression of siRNA or short hairpin RNA (shRNA) driven by U6 promoter effectively mediates target mRNA degradation in mammalian cells. Synthetic siRNA duplexes and plasmid-derived siRNAs can inhibit HIV-1 infection and replication by specifically degrading HIV genomic RNA. McManus et al., J. Immunol. 169:5754–5760; Jacque et al., 2002, Nature 418:435–438; Novina et al., 2002, Nat Med 8:681–686. Also, siRNA targeting HCV genomic RNA inhibits HCV replication. Randall et al., 2003, Proc Natl Acad Sci USA 100:235–240; Wilson et al., 2003, Proc Natl Acad Sci USA 100: 2783–2788. Fas targeted by siRNA protects the liver from fulminant hepatitis and fibrosis. Song et al., 2003, Nat Med 9:347–351. However, the possibility that RNA interference might inhibit HBV replication has not been known until the present invention.

shRNA duplexes specifically target DR elements and regions encoding HBV proteins and are capable of inhibiting HBV replication by degradation of viral RNA species. A series of shRNA expression plasmids were generated. The synthetic DNA oligos encoding shRNAs were annealed and cloned downstream of U6 promoter for the expression of double-stranded shRNA (FIG. 2A). Paul et al., 2002, Nat Biotechnol 20:505–508. These shRNAs' target sites on the HBV RNAs are shown in FIG. 1B. 87i targets the ORF of PreS and Polymerase. 157i, 451i, 660i and 736i target the ORF of S and polymerase, including the nucleotide analog drugs' target sites (660i and 736i). Fu et al., 1998, Biochem Pharmacol 55:1567–1572. 1592i and 1826i target the ORF of X, and the DR2 and DR1 elements in the pregenomic RNA respectively. 1694i targets the ORF of X, and 2310i targets the ORF of core and polymerase in the pregenomic RNA. 2979i targets the polymerase and PreS coding region. The empty vector or shRNA expression vectors were transfected into HepG2 cells and shRNA stably-expressed cells were obtained by selection with G418. pHBV, a plasmid containing HBV-adr genome for generation of HBV virus, and luciferase expression plasmid pJDM1948 were cotransfected into HepG2 cells. Fu et al., 1997, Chin. J. Virol. 13:215–223. The total RNA was isolated 36 hours post-transfection and reverse-transcription PCR experiments were performed. The HBV RNA and luciferase mRNA was quantified by real-time RT-PCR. The expressed shRNAs markedly reduced the HBV RNA level (FIG. 2B). The stably-expressed 87i, 451i, 1592i, 1826i and 2310i reduced HBV RNA by up to 80%, while the other stably-expressed siRNAs reduced HBV RNA by over 90% (FIG. 2B). The stably-expressed siRNAs are potent agents for the cleavage of HBV RNA, which inhibit HBV replication.

Replication assays were performed to determine the effectiveness of the siRNA. The stable cells 157i, 736i, 1592i, 1694i and 1826i were cotransfected with pHBV and pJM1948. The cells were harvested 72 hours post-transfection and lysed without breaking HBV particles. A small fraction of cell lysates was used for the measurement of luciferase activity using a luciferase kit (Promega, Wis.). The HBV DNA in the core particles was isolated from the remaining cell lysates and quantified by real-time PCR. He et al., 2002, Biochem Biophys Res Commun 295:1102–1107. The HBV titer was then normalized with luciferase activity. All the stably-expressed shRNAs potently inhibited HBV replication. The relative HBV titer generally dropped by 90% to 98% (FIG. 2C).

In a specific embodiment, shRNA may be combined with current anti-HBV drugs to increase the anti-HBV efficacy. To test whether shRNA with lamivudine has synergistic effects on the inhibition of HBV replication, pHBV and pJDM1948 were cotransfected into the stably-expressed shRNA cells to observe HBV replication. After transfection, lamivudine was put in the culture medium and maintained for 6 days. It was found that shRNA combined with lamivudine (3TC) exhibited synergic effects to inhibit HBV replication (FIG. 3). In a typical experiments, shRNA with lamivudine reduced HBV titer four times more than lamivudine alone, and two times more than shRNA alone.

Our findings provide evidence for the development of an anti-HBV gene therapy using proper gene delivery vectors, which may enhance the anti-HBV efficacy and overcome drug resistance.

The new therapy can also be combined with chemotherapy. RNAi can specifically silence gene expression through repression of translation when the anti-sense strand in the dsRNA is incompletely paired with the target RNA, or by mediation of target RNA cleavage when the anti-sense strand in the dsRNA is completely paired with the target RNA. A point mutation in HBV genome leads to drug resistance. Stably-expressed shRNAs targeting either drug binding sites (736i), the ORF of S antigene and polymerase (157i), the ORF of X protein (1694i), or the DR elements on the pregenomic RNA (1592i and 1826i), block HBV replication. shRNA stably-expressed cells treated with lamivudine exhibited synergistic effects on the inhibition of HBV replication. Long-term expression of shRNA mediated by viral gene delivery vector will have a great potential in anti-HBV gene therapy, and can be used in the combination therapy with the nucleotide analogs.

5.2. Methods for Inhibiting Gene Expression

Targeted inhibition of gene expression may be implemented via the use of polynucleotide compounds, such as but not limited to, antisense polynucleotides, ribozymes, RNA interference molecules, triple helix polynucleotides and the like, where the nucleotide sequence of such compounds are related to the nucleotide sequences of DNA and/or RNA of genes that are involved in the initiation, transcription, translation or replication. Antisense technology has been the most commonly described approach in protocols to achieve gene-specific interference. For antisense strategies, stoichiometric amounts of single-stranded nucleic acid complementary to the messenger RNA for the gene of interest are introduced into the cell. Another method for engineered interference is based on a triple helical nucleic acid structure. This approach relies on the ability of certain nucleic acid populations to adopt a triple-stranded structure.

In preferred embodiments, an RNA interference (RNAi) molecule is used to decrease gene expression in HBV. RNA interference (RNAi) refers to the use of double-stranded RNA (dsRNA) or small interfering RNA (siRNA) to suppress the expression of a gene comprising a related nucleotide sequence. RNAi is also called post-transcriptional gene silencing (or PTGS). Since the only RNA molecules normally found in the cytoplasm of a cell are molecules of single-stranded mRNA, the cell has enzymes that recognize and cut dsRNA into fragments containing 21–25 base pairs (approximately two turns of a double helix and which are referred to as small interfering RNA or siRNA). The antisense strand of the fragment separates enough from the sense strand so that it hybridizes with the complementary sense sequence on a molecule of endogenous cellular mRNA. This hybridization triggers cutting of the mRNA in the double-stranded region, thus destroying its ability to be translated into a polypeptide. Introducing dsRNA corresponding to a particular gene thus knocks out the cell's own expression of that gene in particular tissues and/or at a chosen time.

Double-stranded (ds) RNA can be used to interfere with gene expression in mammals. dsRNA is used as inhibitory RNA or RNAi of the function of a nucleic acid molecule of the invention to produce a phenotype that is the same as that of a null mutant of a nucleic acid molecule of the invention (Wianny & Zernicka-Goetz, 2000, Nature Cell Biology 2: 70–75).

Alternatively, siRNA can be introduced directly into a cell to mediate RNA interference (Elbashir et al., 2001, Nature 411:494–498). Many methods have been developed to make siRNA, e.g., chemical synthesis or in vitro transcription. Once made, the siRNAs are introduced into cells via transient transfection. A number of expression vectors have also been developed to continually express siRNAs in transiently and stably transfected mammalian cells (Brummelkamp et al., 2002 Science 296:550–553; Sui et al., 2002, PNAS 99(6):5515–5520; Paul et al., 2002, Nature Biotechnol. 20:505–508). Some of these vectors have been engineered to express small hairpin RNAs (shRNAs), which get processed in vivo into siRNA-like molecules capable of carrying out gene-specific silencing. Another type of siRNA expression vector encodes the sense and antisense siRNA strands under control of separate pol III promoters (Miyagishi and Taira, 2002, Nature Biotechnol. 20:497–500). The siRNA strands from this vector, like the shRNAs of the other vectors, have 3' thymidine termination signals. Silencing efficacy by both types of expression vectors was comparable to that induced by transiently transfecting siRNA.

The RNA may comprise one or more strands of polymerized ribonucleotide. It may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition while avoiding a general panic response in some organisms which is generated by dsRNA. Likewise, bases may be modified to block the activity of adenosine deaminase. RNA may be produced enzymatically or by partial/total organic synthesis, any modified ribonucleotide can be introduced by in vitro enzymatic or organic synthesis.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition. The RNA molecule may be at least 10, 12, 15, 20, 21, 22, 23, 24, 25, 30, nucleotides in length.

RNA containing a nucleotide sequences identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12–16 hours; followed by washing). The length of the identical nucleotide sequences may be at least 25, 50, 100, 200, 300 or 400 bases.

One hundred percent sequence identity between the RNA and the target gene is not required to practice the present invention. Thus the invention has the advantage of being able to tolerate sequence variations that might be expected due to genetic mutation, strain polymorphism, or evolutionary divergence.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see also WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

RNA may be directly introduced into the cell (i.e., intracellularly); or introduced extracellularly into a cavity, interstitial space, into the circulation of an organism, introduced orally, or may be introduced by bathing an organism in a solution containing the RNA. Physical methods of introducing nucleic acids, for example, injection directly into the cell or extracellular injection into the organism, may also be used. Vascular or extravascular circulation, the blood or lymph system, and the cerebrospinal fluid are sites where the RNA may be introduced.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, promote annealing of the duplex strands, stabilize the annealed strands, or otherwise increase inhibition of the target gene.

The present invention may be used to introduce RNA into a cell for the treatment or prevention of disease. For example, dsRNA may be introduced into a cancerous cell or tumor and thereby inhibit gene expression of a gene required for maintenance of the carcinogenic/tumorigenic phenotype. To prevent a disease or other pathology, a target gene may be selected which is required for initiation or maintenance of the disease/pathology. Treatment would include amelioration of any symptom associated with the disease or clinical indication associated with the pathology.

Another utility of the present invention is a method of identifying gene function in an organism comprising the use of double-stranded RNA to inhibit the activity of a target gene of previously unknown function. Instead of the time consuming and laborious isolation of mutants by traditional genetic screening, functional genomics would envision determining the function of uncharacterized genes by employing the invention to reduce the amount and/or alter the timing of target gene activity. The invention could be used in determining potential targets for pharmaceuticals, understanding normal and pathological events associated with development, determining signaling pathways responsible for postnatal development/aging, and the like. The increasing speed of acquiring nucleotide sequence information from genomic and expressed gene sources, can be coupled with the invention to determine gene function in an organism.

A simple assay would be to inhibit gene expression according to the partial sequence available from an expressed sequence tag (EST) of HBV. Functional alterations in growth, development, metabolism, disease resistance, or other biological processes would be indicative of the normal role of the EST's gene product.

Useful dsRNS of the present invention may be identified using high throughput screening (HTS). For example, duplex RNA can be produced by an amplification reaction using primers flanking the inserts of any gene library derived from the HBV virus. Inserts may be derived from genomic RNA or mRNA (e.g., cDNA and cRNA). Individual clones from the library can be replicated and then isolated in separate reactions, but preferably the library is maintained in individual reaction vessels (e.g., a 96-well microtiter plate) to minimize the number of steps required to practice the invention and to allow automation of the process. Solutions containing duplex RNAs that are capable of inhibiting the different expressed genes can be placed into individual wells positioned on a microtiter plate as an ordered array, and intact cells/organisms in each well can be assayed for any changes or modifications in behavior or development due to inhibition of target gene activity. The amplified RNA can be injected into, the cell/organism containing the target gene. Alternatively, the duplex RNA can be produced by in vivo or in vitro transcription from an expression construct used to produce the library. The construct can be replicated as individual clones of the library and transcribed to produce the RNA; each clone can then be injected into, the cell/organism containing the target gene. The function of the target gene can be assayed from the effects it has on the cell/organism when gene activity is inhibited. This screening could be amenable to small subjects that can be processed in large number, for example: viruses and tissue culture cells derived from mammals.

5.3. Assay for Measuring Inhibition of Gene Expression

Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

5.4. Prophylactic and Therapeutic Agents

According to the invention, therapy by administration of the RNA molecules of the present invention is combined with the administration of one or more therapies such as, but not limited to, chemotherapies, radiation therapies, hormonal therapies, and/or biological therapies/immunotherapies.

In a specific embodiment, the methods of the invention encompass the administration of angiogenesis inhibitors such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Additional examples of anti-cancer agents that can be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D;

antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor.

In more particular embodiments, the present invention also comprises the administration of the RNA molecules of the present invention in combination with the administration of one or more therapies such as, but not limited to anti-cancer agents such as those disclosed in Table I, preferably for the treatment of liver cancers.

TABLE 1

| Therapeutic Agent | Dose/Administration/Formulation | | |
|---|---|---|---|
| doxorubicin hydrochloride (Adriamycin RDF ® and Adriamycin PFS ®) | Intravenous | 60–75 mg/m$^2$ on Day 1 | 21 day intervals |
| epirubicin hydrochloride (Ellence ™) | Intravenous | 100–120 mg/m$^2$ on Day 1 of each cycle or divided equally and given on Days 1–8 of the cycle | 3–4 week cycles |
| fluorousacil | Intravenous | How supplied: 5 mL and 10 mL vials (containing 250 and 500 mg flourouracil respectively) | |
| docetaxel (Taxotere ®) | Intravenous | 60–100 mg/m$^2$ over 1 hour | Once every 3 weeks |
| paclitaxel (Taxol ®) | Intravenous | 175 mg/m$^2$ over 3 hours | Every 3 weeks for 4 courses (administered sequentially to doxorubicin-containing combination chemotherapy) |
| tamoxifen citrate (Nolvadex ®) | Oral (tablet) | 20–40 mg Dosages greater than 20 mg should be given in divided doses (morning and evening) | Daily |
| leucovorin calcium for injection | Intravenous or intramuscular injection | How supplied: 350 mg vial | Dosage is unclear from text. PDR 3610 |
| luprolide acetate (Lupron ®) | Single subcutaneous injection | 1 mg (0.2 mL or 20 unit mark) | Once a day |
| flutamide (Eulexin ®) | Oral (capsule) | 250 mg (capsules contain 125 mg flutamide each) | 3 times a day at 8 hour intervals (total daily dosage 750 mg) |
| nilutamide (Nilandron ®) | Oral (tablet) | 300 mg or 150 mg (tablets contain 50 or 150 mg nilutamide each) | 300 mg once a day for 30 days followed by 150 mg once a day |
| bicalutamide (Casodex ®) | Oral (tablet) | 50 mg (tablets contain 50 mg bicalutamide each) | Once a day |
| progesterone | Injection | USP in sesame oil 50 mg/mL | |
| ketoconazole (Nizoral ®) | Creme | % creme applied once or twice daily depending on symptoms | |
| prednisone | Oral (tablet) | Initial dosage may vary from 5 mg to 60 mg per day depending on the specific disease entity being treated. | |
| estramustine phosphate sodium (Emcyt ®) | Oral (capsule) | 14 mg/kg of body weight (i.e. one 140 mg capsule for each 10 kg or 22 lb of body weight) | Daily given in 3 or 4 divided doses |
| etoposide or VP-16 | Intravenous | 5 mL of 20 mg/mL solution (100 mg) | |
| dacarbazine (DTIC-Dome ®) | Intravenous | 2–4.5 mg/kg | Once a day for 10 days. May be repeated at 4 week intervals |
| polifeprosan 20 with carmustine implant (BCNU) (nitrosourea) (Gliadel ®) | wafer placed in resection cavity | 8 wafers, each containing 7.7 mg of carmustine, for a total of 61.6 mg, if size and shape of resection cavity allows | |
| cisplatin | Injection | [n/a in PDR 861] How supplied: solution of 1 mg/mL in multi-dose vials of 50 mL and 100 mL | |
| mitomycin | Injection | supplied in 5 mg and 20 mg vials (containing 5 mg and 20 mg mitomycin) | |
| gemcitabine HCl (Gemzar ®) | Intravenous | For NSCLC- 2 schedules have been investigated and the optimum schedule has not been determined 4 week schedule- administration intravenously at 1000 mg/m$^2$ over 30 minutes on 3 week schedule- Gemzar administered intravenously at 1250 mg/m$^2$ over 30 minutes | 4 week schedule Days 1, 8 and 15 of each 28-day cycle. Cisplatin intravenously at 100 mg/m$^2$ on day 1 after the infusion of Gemzar. 3 week schedule- Days 1 and 8 of each 21 day cycle. Cisplatin at dosage of 100 mg/m$^2$ administered intravenously after administration of Gemzar on day 1. |

TABLE 1-continued

| Therapeutic Agent | | Dose/Administration/Formulation | |
|---|---|---|---|
| carboplatin (Paraplatin ®) | Intravenous | Single agent therapy: 360 mg/m² I.V. on day 1 (infusion lasting 15 minutes or longer) Other dosage calculations: Combination therapy with cyclophosphamide, Dose adjustment recommendations, Formula dosing, etc. | Every 4 weeks |
| ifosamide (Ifex ®) | Intravenous | 1.2 g/m² daily | 5 consecutive days Repeat every 3 weeks or after recovery from hematologic toxicity |
| topotecan hydrochloride (Hycamtin ®) | Intravenous | 1.5 mg/m² by intravenous infusion over 30 minutes daily | 5 consecutive days, starting on day 1 of 21 day course |

The invention also encompasses administration of the RNA molecules of the present invention in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radiaoactive source is placed inside the body close to cancer cells or a tumor mass.

Cancer therapies and their dosages, routes of administration and recommended usage are known in the art and have been described in such literature as the *Physician's Desk Reference* (56th ed., 2002).

5.5. Characterization and Demonstration of Therapeutic or Prophylactic Utility Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.6. Demonstration of Therapeutic Utility

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed. A lower level of proliferation or survival of the contacted cells indicates that the therapeutic agent is effective to treat the condition in the patient. Alternatively, instead of culturing cells from a patient, therapeutic agents and methods may be screened using cells of a tumor or malignant cell line or an endothelial cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

Compounds for use in therapy can be tested in suitable animal model systems prior to testing in humans, including but not limited to in rats, mice, chicken, cows, monkeys, rabbits, hamsters, etc.

The principle animal models for known in the art and widely used are known and described in the art as described above.

Further, any assays known to those skilled in the art can be used to evaluate the prophylactic and/or therapeutic utility of the combinatorial therapies disclosed herein for treatment or prevention of cancer.

5.7. Pharmaceutical Compositions

The compositions of the invention include bulk drug compositions useful in the manufacture of pharmaceutical compositions (e.g., impure or non-sterile compositions) and pharmaceutical compositions (i.e. , compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of RNA molecules of the present invention and/or an anti-cancer agent, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Various delivery systems are known and can be used to administer the RNA molecules of the present invention or the combination of the RNA molecules of the present invention and a prophylactic agent or therapeutic agent useful for preventing or treating cancer, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429–4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural, and mucosal (e.g., intranasal and oral routes). In a specific embodiment, prophylactic or therapeutic agents of the invention are administered intramuscularly, intravenously, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

In yet another embodiment, the prophylactic or therapeutic agent can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the antibodies of the invention or fragments thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115–138 (1984)).

Controlled release systems are discussed in the review by Langer (1990, Science 249:1527–1533). Any technique known to one of skill in the art can be used to produce sustained release formulations comprising one or more therapeutic agents of the invention. See, e.g., U.S. Pat. No. 4,526,938, PCT publication WO 91/05548, PCT publication WO 96/20698, Ning et al., 1996, "Intratumoral Radioimmunotheraphy of a Human Colon Cancer Xenograft Using a Sustained-Release Gel," Radiotherapy & Oncology 39:179–189, Song et al., 1995, "Antibody Mediated Lung Targeting of Long-Circulating Emulsions," PDA Journal of Pharmaceutical Science & Technology 50:372–397, Cleek et al., 1997, "Biodegradable Polymeric Carriers for a bFGF Antibody for Cardiovascular Application," Pro. Int'l. Symp.

Control. Rel. Bioact. Mater. 24:853–854, and Lam et al., 1997, "Microencapsulation of Recombinant Humanized Monoclonal Antibody for Local Delivery," Proc. Int'l. Symp. Control Rel. Bioact. Mater. 24:759–760, each of which is incorporated herein by reference in their entirety.

5.7.1. Formulations

Pharmaceutical compositions for use in accordance with the present invention may be formulated in conventional manner using one or more physiologically acceptable carriers or excipients.

Thus, the RNA molecules of the present invention or other anti-cancer agents and their physiologically acceptable salts and solvates may be formulated for administration by inhalation or insufflation (either through the mouth or the nose) or oral, parenteral or mucosol (such as buccal, vaginal, rectal, sublingual) administration. In a preferred embodiment, local or systemic parenteral administration is used.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents ( e.g., sorbitol syrup, cellulose derivatives or hydrogenated edible fats); emulsifying agents (e.g. , lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the prophylactic or therapeutic agents for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The prophylactic or therapeutic agents may be formulated for parenteral administration by injection, e.g. , by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The prophylactic or therapeutic agents may also be formulated in rectal compositions such as suppositories or retention enemas, e.g., containing conventional suppository bases such as cocoa butter or other glycerides.

In addition to the formulations described previously, the prophylactic or therapeutic agents may also be formulated as a depot preparation. Such long acting formulations may be administered by implantation (for example subcutaneously or intramuscularly) or by intramuscular injection. Thus, for example, the prophylactic or therapeutic agents may be formulated with suitable polymeric or hydrophobic materials (for example as an emulsion in an acceptable oil) or ion exchange resins, or as sparingly soluble derivatives, for example, as a sparingly soluble salt.

The invention also provides that a prophylactic or therapeutic agent is packaged in a hermetically sealed container such as an ampoule or sachette indicating the quantity. In one embodiment, the prophylactic or therapeutic agent is supplied as a dry sterilized lyophilized powder or water free concentrate in a hermetically sealed container and can be reconstituted, e.g., with water or saline to the appropriate concentration for administration to a subject.

In a preferred embodiment of the invention, the formulation and administration of various chemotherapeutic, biological/immunotherapeutic and hormonal therapeutic agents are known in the art and often described in the *Physician's Desk Reference*, 56$^{th}$ ed. (2002). For instance, in certain specific embodiments of the invention, the therapeutic agents of the invention can be formulated and supplied as provided in Table 1.

In other embodiments of the invention, radiation therapy agents such as radioactive isotopes can be given orally as liquids in capsules or as a drink. Radioactive isotopes can also be formulated for intravenous injections. The skilled oncologist can determine the preferred formulation and route of administration.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

In certain preferred embodiments, the pack or dispenser contains one or more unit dosage forms containing no more than the recommended dosage formulation as determined in the *Physician's Desk Reference* (56$^{th}$ ed. 2002, herein incorporated by reference in its entirety) for a particular cancer therapy.

5.7.2. Dosages

The amount of the composition of the invention which will be effective in the treatment, prevention or management of diseases related to HBV including, but not limited to cancer, can be determined by standard research techniques. For example, the dosage of the composition which will be effective in the treatment, prevention or management of a disease can be determined by administering the composition to an animal model such as, e.g., the animal models disclosed herein or known to those skilled in the art. In addition, in vitro assays may optionally be employed to help identify optimal dosage ranges.

Selection of the preferred effective dose can be determined (e.g., via clinical trials) by a skilled artisan based upon the consideration of several factors which will be known to one of ordinary skill in the art. Such factors include the disease to be treated or prevented, the symptoms involved, the patient's body mass, the patient's immune status and other factors known by the skilled artisan to reflect the accuracy of administered pharmaceutical compositions.

The precise dose to be employed in the formulation will also depend on the route of administration, and the seriousness of the cancer, and should be decided according to the judgment of the practitioner and each patients circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human and humanized antibodies have a longer half-life within the human body than antibodies from other species due to the immune response to the foreign polypeptides. Thus, lower dosages of human antibodies and less frequent administration is often possible.

For other cancer therapeutic agents administered to a patient, the typical doses of various cancer therapeutics known in the art are provided in Table 1. Given the invention, certain preferred embodiments will encompass the administration of lower dosages in combination treatment regiments than dosages recommended for the administration of single agents.

The invention provides for any method of administrating lower doses of known prophylactic or therapeutic agents than previously thought to be effective for the prevention, treatment, management or amelioration of cancer. Preferably, lower doses of known anti-cancer therapies are administered in combination with lower doses of the RNA molecule of the present invention.

5.8. Kits

The invention provides a pharmaceutical pack or kit comprising one or more containers filled with the RNA molecules of the present invention and one or more other prophylactic or therapeutic agents useful for the treatment of a cancer. The invention also provides a pharmaceutical pack or kit comprising one or more containers filled with one or more of the ingredients of the pharmaceutical compositions of the invention. Optionally associated with such container (s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises the RNA molecules of the present invention, in one or more containers, and one or more other prophylactic or therapeutic agents useful for the treatment of cancer, in one or more containers. In certain preferred embodiments, the other prophylactic or therapeutic agent is a chemotherapeutic. In certain preferred embodiments, the prophylactic or therapeutic agent is a biological or hormonal therapeutic. In certain preferred embodiments, the other prophylactic or therapeutic agent is a chemotherapeutic. In other preferred embodiments, the other prophylactic or therapeutic agent is a biological or hormonal therapeutic.

5.9. Gene Therapy

Gene therapy refers to treatment or prevention methods performed by the administration of a nucleic acid to a subject. In this embodiment of the invention, the therapeutic nucleic acid produces intracellularly a RNA molecule of the present invention that mediates a therapeutic effect by inhibiting gene expression. In another embodiment, nucleic acids comprising a sequence encoding the RNA molecules of the present invention are administered to inhibit HBV gene in the cell.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5): 155–215). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds.), 1994, Current Protocols in Human Genetics, John Wiley & Sons, NY.

Delivery of the nucleic acid into a patient may be either direct, in which case the patient is directly exposed to the nucleic acid or nucleic acid-carrying vector or a delivery complex, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the RNA molecules of the present invention. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection, or by use of microparticle bombardment (e.g., a gene gun; Biolistic, Dupont), or coating with lipids or cell-surface receptors or transfecting agents, encapsulation in biopolymers (e.g., see U.S. Pat. No. 5,635,493), encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342: 435–438).

In a specific embodiment, a viral vector that expresses the RNA molecules of the present invention is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The RNA molecules of the present invention to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234.

Adeno-associated virus (AAV) has also been proposed for use in gene therapy (Walsh et al., 1993, Proc. Soc. Exp. Biol. Med. 204:289–300.

Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92). The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, recombinant blood cells (e.g., hematopoietic stem or progenitor cells) are preferably administered intravenously.

6. EXAMPLES

Constructs pAVU6+27, which contains human U6 promoter and the first 27-bp of U6 RNA coding sequence, has been described by Paul et al., 2002, Nat Biotechnol 20:505–508. A series of shRNA expression vectors was generated by inserting annealed oligos containing sense-TTCG-antisense sequence into pAVU6+27 vector between Sal I and Xba I sites.

The oligo sequences coding for the sense strand of shRNA were:

```
87i,
5'-GACTACTGCCTCACCCATA-3';           (SEQ ID NO: 1)

157i,
5'-CATGGAGAGCACAACATCA-3';           (SEQ ID NO: 2)

451i,
5'-GACTACCAAGGTATGTTGC-3';           (SEQ ID NO: 3)

660i,
5'-CGTTTCGCCTGGCTCAGTT-3';           (SEQ ID NO: 4)

736i,
5'-GTTATATGGATGATGTGGT-3';           (SEQ ID NO: 5)

1593i,
5'-TTCACCTCTGCACGTCGCA-3'            (SEQ ID NO: 6)
(target DR2);

1694i,
5'-GACCTTGAGGCATACTTCA-3';           (SEQ ID NO: 7)

1826i,
5'-TTCACCTCTGCCTAATCAT-3'            (SEQ ID NO: 8)
(target DR1);

2310,
5'-GTTGATAAGATAGGGGCAT-3'; and       (SEQ ID NO: 9)

2979i,
5'-ACTTCAACCCCAA CAAGG-3'.           (SEQ ID NO: 10)
```

Cell Culture, Transfection, and Reporter Gene Assays

HepG2 cells were grown in DMEM with 10% fetal bovine serum in 10-cm dishes. Transfections were carried out using Lipofectamine 2000 reagent (Invitrogen, MD) as described in the manufacturer's instructions. The transfected cells were selected with 500 µg/ml of G418 for three weeks with medium changes every three days. The cells for the stable expression of shRNA were used for HBV replication assay.

To detect the effects of stably-expressed shRNA on HBV RNA degradation and replication, HepG2 cells were cotransfected with 100 ng of luciferase expression plasmid pJMD1948 (He et al., 1999, Proc Natl Acad Sci USA 96:10212–10217) and 900 ng of pHBV (Fu et al., 1998, Biochem Pharmacol 55:1567–1572; Fu et al., 1997, Chin J. Virol., 13:215–223) in each well of 12-well plates. Luciferase activities were determined after 72 hrs using a luciferase detection kit (Promega, Wis.). The HBV titers were normalized by luciferase activities. To test the synergistic effects of shRNA and lamivudine (3TC), the shRNA stable-expression cells cotransfected with pHBV and pJDM1948 were culture in 3TC containing medium (0.5 µM) and harvested after 6-day incubation with fresh medium change every two days.

Quantitative PCR Analysis

Real-time PCR was performed to quantify HBV viral genomic DNA or mRNA using an HBV diagnostic kit (PG Biotech. Ltd., Shenzheng, China) described previously. He et al., 2002, Biochem Biophys Res Commun 295:1102–1107. For measurement of viral genomic DNA, HepG2 cells were harvested 72 hrs post-transfection and lysed in 200 µl of lysis buffer (PBS with 1% NP-40 and cocktail protein inhibitors). The luciferase activities were determined using 25 µl of cell lysates. The remaining cell lysates were treated with DNase I (final conc. 1 mg/ml) at 37° C. for 60 min to remove the transfected plasmid DNA before the isolation of HBV genomic DNA from core particles. To quantify the mRNA of HBV, the total mRNA was isolated using Trizol reagent (Invitrogen, MD) and reverse-transcribed (RT) to cDNA using oligo dT primimg. Quantitative RT-PCR experiments were carried out and the values were normalized with luciferase mRNA (internal control). To quantify luciferase mRNA (internal control), primer 5'-GCGACCAACGCCTTAGATTG CAA-3' (Luc_F) (SEQ ID NO:11), 5'-GCGGTCAACG ATGAA-GAAGTG-3' (Luc_R) (SEQ ID NO:12) and probe 5'-FAM-ATGGATGGCTACATTCTGGA GACATAG-TAMRA-3' (SEQ ID NO:13) were used in the real-time PCR reactions.

7. Equivalents

Those skilled in the art will recognize, or be able to ascertain many equivalents to the specific embodiments of the invention described herein using no more than routine experimentation. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

What is claimed is:

1. An isolated nucleic acid molecule comprising the nucleotide sequence of SEQ ID NO:1, 2, 3, 4, 7, or 10, or a complement thereof.

2. The nucleic acid molecule of claim 1 wherein said nucleic acid molecule is double-stranded.

3. The nucleic acid molecule of claim 2 wherein said nucleic acid molecule is a RNA.

4. A vector comprising the nucleic acid molecule of claim 1.

5. The vector of claim 4, wherein said nucleic acid molecule is operatively linked to human U6 promoter.

6. The vector of claim 4, wherein said nucleic acid molecule comprises a sence-TTCG-antisense sequence of said nucleotide sequence.

7. The isolated nucleic acid molecule of claim 1, wherein said nucleic acid molecule comprises a sence-TTCG-antisense sequence of said nucleotide sequence.

8. The nucleic acid molecule of claim 7, wherein said nucleic acid molecule is a RNA.

9. A method of inhibiting expression of a target gene of HBV in a host cell in vitro, comprising administering to the host cell the nucleic acid molecule of claim 1.

* * * * *

SEQUENCE LISTING

```
<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gactactgcc tcacccata                                                19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
catggagagc acaacatca                                                19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gactaccaag gtatgttgc                                                19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgtttcgcct ggctcagtt                                                19

<210> SEQ ID NO 5
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gttatatgga tgatgtggt                                               19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttcacctctg cacgtcgca                                               19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaccttgagg catacttca                                               19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttcacctctg cctaatcat                                               19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gttgataaga tagggcat                                                19

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
acttcaaccc caacaagg                                                18

<210> SEQ ID NO 11
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 11
gcgaccaacg ccttagattg caa                                              23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 12
gcggtcaacg atgaagaagt g                                                21

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 13
atggatggct acattctgga gacatag                                          27
```